United States Patent [19]

Oswald

[11] 4,005,546
[45] Feb. 1, 1977

[54] METHOD OF WASTE TREATMENT AND ALGAE RECOVERY

[75] Inventor: William J. Oswald, Concord, Calif.

[73] Assignee: The Regents of the University of California, Berkeley, Calif.

[22] Filed: July 21, 1975

[21] Appl. No.: 597,437

[52] U.S. Cl. .................................. 47/1.4; 210/11
[51] Int. Cl.² ................... C02C 1/00; A01G 31/00
[58] Field of Search ............................ 210/2–18; 47/1.4, 58

[56] References Cited

UNITED STATES PATENTS

| | | | |
|---|---|---|---|
| 3,429,806 | 2/1969 | Carter et al. | 210/3 |
| 3,431,200 | 3/1969 | Davis et al. | 47/1.4 |
| 3,462,360 | 8/1969 | McKinney | 210/11 |
| 3,546,812 | 12/1970 | Kobayashi et al. | 47/1.4 |
| 3,598,726 | 8/1971 | Welch | 210/3 |
| 3,645,040 | 2/1972 | Ort | 47/1.4 |
| 3,732,089 | 5/1973 | Megronigle | 47/1.4 X |
| 3,768,200 | 10/1973 | Klock | 47/1.4 |

OTHER PUBLICATIONS

Algal Culture from Laboratory to Pilot Plant, Burlew, Carnegie Inst. of Wash. Publ. No. 600, 1953, pp. 107, 113, 143–152, 194, relied on.

*Primary Examiner*—Robert E. Bagwill
*Attorney, Agent, or Firm*—Lothrop & West

[57] ABSTRACT

A method of waste treatment and algae recovery involves making available in a first pond open to light and air a first body of waste water such as sewage containing algae, the algae growing on the contained nutrients. The first body is retained under natural culture conditions for a predetermined detention period, usually several days, and is then transferred to a second pond as a second body open to light and air. To the second body some normal algal nutrients are added and more particularly the body is continuously agitated at a moderate rate to maintain the growing algae in suspension. Preferably, to the second body and with the nutrients, there is added an amount of lime insufficient to cause coagulation of the algae. After a predetermined detention time of several days in the second, mixing pond the mixed material is transferred to a third pond. The third pond is shielded from the light and is dark. The third pond is unagitated and is quiet. The algae therein readily separate by gravity to the bottom of the pond. The remaining relatively clean, supernatant liquid is withdrawn at the top while the settled algae are removed from the bottom. Some of the removed algae may be recirculated to the first pond for inoculation.

11 Claims, 1 Drawing Figure

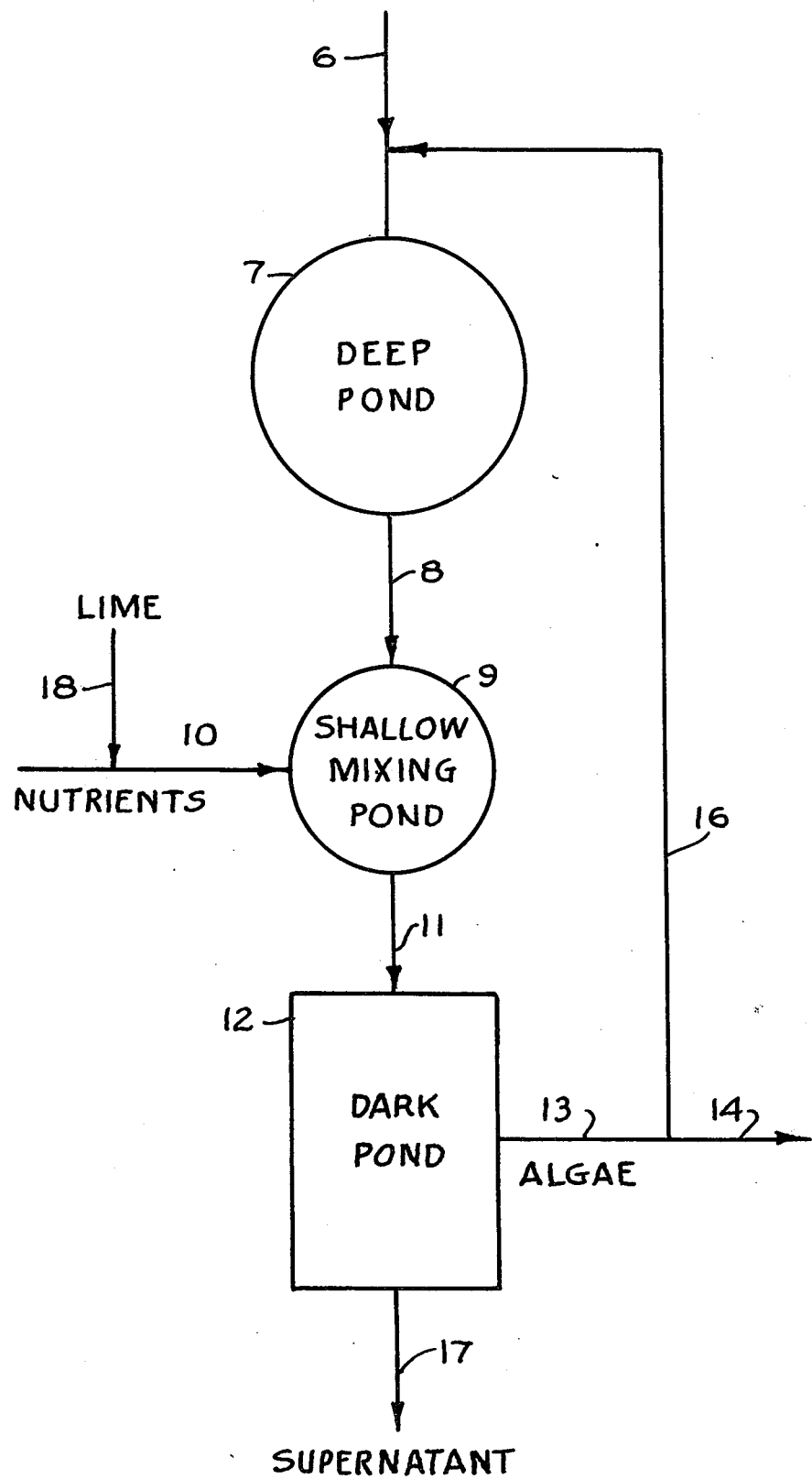

METHOD OF WASTE TREATMENT AND ALGAE RECOVERY

There is a growing need for the treatment of waste water, more particularly outfall sewage, not only for the recovery of the materials therein as having value but more particularly to prevent such materials being discharged into other waters and contaminating them. It has long been known that algae, particularly those that occur naturally in such waste water, when appropriately cultured, are effective in removing many and in some instances nearly all of the contaminants in the waste water. However, it is extremely difficult then to remove the algae from the treated water. But the algae must be removed since otherwise the algae themselves become contaminants in the discharge. It is hard to separate the algae from the water to be discharged in any economical fashion. Algae have been removed in part by centrifugation, but that is a very expensive and not always effective process. It has also been proposed to precipitate the algae by coagulation with lime, for example. While this is effective to remove virtually all of the algae, it is cumbersome and very expensive since the quantity of lime required may be several times, perhaps four times, the quantity of the algae removed. There is consequently still a need for a simple, effective, economical way of treating waste waters with algae, particularly sewage, in such a fashion as to remove the treating algae and to evolve a relatively clean resulting water.

It is therefore an object of the invention to provide a method of waste water treatment with algae to afford economically and effectively a supply of reclaimed or cleaned water and of usable algae.

Another object of the invention is to provide a method of waste water treatment by algae in which the algae are substantially all easily and cheaply separated from the discharged treated water.

Another object of the invention is to provide a method of waste water treatment with algae in which the algae are conditioned to precipitate readily from their containing medium.

Another object of the invention is to provide a method of waste treatment involving algae in which the equipment and land areas required are economical.

A further object of the invention is to provide a method of waste treatment that can readily be managed and supervised without highly specialized skills.

Another object of the invention is in general to provide an improved method of waste water treatment also affording recovery of algae.

Other objects, together with the foregoing, are attained by the practice of the method as described in the accompanying description and illustrated in the accompanying drawing, in which:

The FIG. is a flow diagram illustrating the method of the invention.

While all of the fine scale parameters of the instant method are not yet known, the method has been practiced long enough and well enough to afford indications of its major boundaries and requirements. Speaking generally, waste material such as sewage in water containing naturally occurring algae is first confined in a facultative pond open to light and air and in which the algae propagate without the special addition of nutrients. This occurs for a predetermined detention period. Then the detained material is transferred from this first pond to a second pond, also open to light and air. Therein the material is detained for another predetermined period. In the second pond the contents are continuously agitated at a relatively slow rate in order that the contained algae be maintained suspended and so that the contents of the second pond are kept largely homogeneous. In the second pond the algae propagate on extra nutrients supplied thereto. In addition, lime may also be added. This is not nearly sufficient to afford coagulation in the usual fashion. After a predetermined detention time in the second pond the contents are removed to a third pond. This is unusual in algal culture in that it is protected from the light. In fact the third pond is dark and is maintained quite quiescent. It has been found that the algae in the third pond, after their continued agitation in the second pond have no buoyancy or surface-seeking trend. They tend to precipitate quite readily in the third pond and separate or settle by gravity to the pond bottom. The liquid is left devoid of virtually all of its original contaminants and is also algae free in the upper reaches thereof. The supernatant liquid is drawn off for use. Masses of precipitated or settled algae are mechanically removed from the third pond bottom, either continuously or from time to time. There can be some recirculation of the algae from the third pond to the first pond.

Of interest herein is the disclosure in Gotaas U.S. Pat. No. 2,867,945 of Jan. 13, 1959 relating to symbiosis of raw sewage and algae.

The process of the invention has been carried out with sewage from the outfall sewer from the city of Richmond, Calif. Such waste material is supplied in this case through a conduit 6 leading into the entrance to a first deep, facultative pond 7. This is formed with earth boundaries in the customary way. It has a depth of approximately of about 3 to 12 meters. The contents of the deep or facultative pond 7 are retained for a predetermined time under natural conditions. The detention time in the pond 7 usually ranges from about 10 to 20 days. During this time the normal algal content of the first body in the first pond 7 grows and propagates in the customary way, relying on sewage nutrients; since the growing and holding conditions in the pond 7 are substantially standard or natural without any particular, artificial addition or subtraction. While many algae may be present naturally in the pond 7 from the influent sewage, it is found that normally the principal algae present are Chlorella and Scenedesmus.

After the detention period of approximately ten to twenty days in the first pond, the contents of such pond are transferred through a conduit 8 to a second pond 9, the contents of the second pond being referred to then as a second body. The pond 9 is constructed like the pond 7 except that it need not be as great in area and is not as great in depth. The second pond is open to light and air in the customary fashion. The customary depth ranges from about 20 to 40 centimeters.

The second pond is particularly characterized as a mixing pond, since the contents thereof are continuously agitated; for example, by stirring paddles or propellers operating at a modest rate, for example, providing a liquid velocity of the order of 15 to 45 cm. per second. All parts of the second body are continuously and steadily agitated, pains being taken not to have any quiet or undisturbed portions in the pond. A rotary stirrer in a circular pond is most effective. As the algae are cultured in the second pond 9 there may be added thereto a supply of the customary nutrients, as represented by the arrow 10 in the FIGURE. The nutrients are sufficient in connection with the open pond so that the algae increase substantially in growth according to well-known curves. It appears also that the algae, being continuously agitated in sundry directions and never being permitted to remain still and quiet under the sole or unidirectional attraction of gravity, tend to lose their orienting ability or their ability slowly to rise toward the pond surface.

After a predetermined detention time in the second pond 9, ranging usually between three and six days, the contents of the second pond; that is, the second body, is transferred therefrom through a conduit 11 into a third pond 12. While the third pond 12 may be formed in the earth just as are the ponds 7 and 9, the third pond differs markedly from the other ponds in that usually it is covered. Its contents are protected from the light by a cover or substantial depth. The pond 12 is a dark pond. Its normal depth range is from about three to ten meters. The third pond contents are now referred to as the third body. The entire contents are maintained for from 1.5 to three days in darkness in the pond 12 and without any agitation or surface rippling so that the third body is quiescent.

It has been found, most surprisingly, that after the continuous, steady agitation in the second pond 9, the contained algae in the third, dark and quiet pond have apparently lost their ability to remain static or to travel upwardly in the surrounding liquid medium. They have sufficient density to settle or precipitate with little difficulty. The internal mechanism or reason for this is not now known, although it may involve interference with vacuole formation and may involve nitrogen, carbon or light deficiency.

The settled or precipitated algae form a coating or layer on the bottom of the third pond 12 by gravital action. They are recovered in some instances by putting the third pond out of service, dewatering it and permitting the algae then to dry in the sun, the cover of the pond being removed for that purpose. The dried algae can be removed mechanically by ordinary earth moving equipment. The recovered algae are useful in many ways as for cattle feed and the like.

Alternatively, the algal contents of the dark pond are withdrawn from the bottom with some carrying liquid through a line 13 leading to a final discharge line 14. Under some circumstances there is a branch line 16 from the discharge line 13 leading back to the inlet 6. Some of the algae in water are recirculated and serve as an addition to or an inoculant for the incoming raw sewage.

Because of the usual excellent separation of algae from the medium in the third pond 12, the supernatant water therein can readily be drawn off through a line 17 and can be discharged for use without causing contamination. During the normal practice of this method the algae themselves consume virtually all of the contaminants in the influent and since they make a ready separation from the medium leave the water to be discharged in excellent and usable condition.

Under some circumstances, however, the output may be variable due to widely ranging differences in input. Under all conditions so far encountered, it has been possible to maintain a uniformly clean output by adding lime to the second pond 9. Lime addition is represented by an arrow 18 and conveniently is accomplished by adding the lime to the ingoing nutrients. The lime quantity involved is much less than is required for algae coagulation. In fact, experience has shown that the addition of a few mg. of lime per liter to material in the second pond 9 is adequate to produce a substantially contaminant-free efflux from the third pond 12. An example of the addition of different quantities of lime and the resulting materials in the water medium is as follows:

| LIME | NITROGEN |
| --- | --- |
| 25 mg./liter | 2/6 gm./liter |
| 50 mg./liter | 1.05 gm./liter |
| 65 mg./liter | 0.93 mg./liter |

The above nitrogen includes organic nitrogen, ammonia nitrogen and nitrate nitrogen. Since most ammonia is removed, little is left later to combine with later treating chlorine so there is little production of toxic chloramines. At the 65 mg./liter rate of lime addition, the phosphorus residue is only 0.1 mg./liter.

The economics of the foregoing arrangement are quite favorable in that the equipment involved is elementary, the ponds are of only normal construction and require reasonable areas and a good complete (tertiary) sewage treatment is given. The motive force, except for the agitation mechanism is largely sunlight. The agitators are mechanically driven but the amount of power requisite to do so is relatively small since the agitation, although continuous, is at a modest rate. If predators such as Daphnia and Rotifera appear in the second pond, they can readily be removed by mechanical screening.

While the third, dark pond does require some protection from light, this is relatively economically and easily accomplished. The result, therefore, is that algae are utilized most effectively in scouring the waste water and removing the contaminants therefrom, not only to supply clean effluent water but likewise themselves readily to be separated and perhaps utilized for cattle feed and the like. There is an economical and dependable removal of BOD, suspended solids, ammonia, nitrate, organic nitrogen, phosphate and infectious agents and an opportunity for reclamation of carbon, nitrogen and phosphorus in the form of algae. The overall result consequently is the provision of a supply of clean water from a contaminated source and the provision of a valuable feed stuff or the like.

What is claimed is:

1. A method of waste treatment and algae recovery comprising making available in a first pond open to light and air a first body of sewage containing algae, retaining said first body under natural culture conditions for from ten to twenty days, then transferring to a second pond as a second body open to light and air at least a portion of said first body, substantially continuously agitating said second body in said second pond for from three to six days, then transferring to a third pond as a third body substantially closed to light at least a portion of said contents of said second pond, retaining said third body quiescent for from one and a half to three days during which algae settle, and removing settled algae from said third pond.

2. A method as in claim 1 including adding lime to said second pond in a quantity much less than the quantity required to coagulate all of said algae in said third pond.

3. A method as in claim 1 in which said first pond has a depth of approximately 3 to 12 meters.

4. A method as in claim 1 in which said second pond has a depth of approximately 20 to 40 cm.

5. A method as in claim 1 in which said third pond has a depth of approximately 3 to 10 meters.

6. A method as in claim 1 in which said second body is agitated at a flow velocity of the order of 15 to 45 cm. per second.

7. A method as in claim 1 including adding lime to said body of waste liquid in the approximate amount of from 25 mg./liter to 65 mg./liter.

8. A method as in claim 7 in which said lime is added to said waste liquid being agitated.

9. A method of waste treatment and algae recovery comprising continuously agitating a body of waste liquid containing algae while subject to light and during a substantial growth period of said algae for a detention period of from three to six days, then holding said body quiet in the absence of light during a substantial settling period of said algae for from one and a half to three days, and then removing settled algae from said body.

10. A method of treating waste liquid containing algae comprising first agitating said waste liquid continuously for several days during algal growth in the light and then immediately thereafter holding said liquid quiet in the dark for several days.

11. A method of algae recovery comprising culturing algae in a liquid medium under natural conditions and with nutrients for normal growth of the algae for from ten to twenty days, then confining a body of said algae and said liquid medium for from three to six days while continuously subjecting said body to agitation in a substantially uniform manner, and then confining said body of algae and medium immediately after said agitation for from one and one-half to three days in the absence of light and with substantial quiet.

* * * * *